United States Patent
Kulkarni et al.

(10) Patent No.: US 11,707,700 B2
(45) Date of Patent: Jul. 25, 2023

(54) PROCESS FOR INTERFACIAL SEPARATION OF METAL NANOPARTICLES OR NANOWIRES USING CENTRIFUGAL SEPARATORS

(71) Applicant: COUNCIL OF SCIENTIFIC & INDUSTRIAL RESEARCH, New Delhi (IN)

(72) Inventors: Amol Arvind Kulkarni, Maharashtra (IN); Jaydeep Bipin Deshpande, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 364 days.

(21) Appl. No.: 16/610,211

(22) PCT Filed: Apr. 30, 2018

(86) PCT No.: PCT/IN2018/050265
§ 371 (c)(1),
(2) Date: Nov. 1, 2019

(87) PCT Pub. No.: WO2018/203347
PCT Pub. Date: Nov. 8, 2018

(65) Prior Publication Data
US 2021/0283532 A1    Sep. 16, 2021

(30) Foreign Application Priority Data
May 1, 2017    (IN) .............................. 201711007178

(51) Int. Cl.
*B01D 21/26* (2006.01)
*B82Y 40/00* (2011.01)

(52) U.S. Cl.
CPC ............ *B01D 21/262* (2013.01); *B82Y 40/00* (2013.01)

(58) Field of Classification Search
None
See application file for complete search history.

(56) References Cited

U.S. PATENT DOCUMENTS

2010/0326891 A1* 12/2010 Wang .................... B82Y 40/00
                                                                    209/132
2011/0003285 A1*  1/2011 Niwa ....................... C07K 1/14
                                                                    435/6.11

(Continued)

FOREIGN PATENT DOCUMENTS

CN        103983632 A        8/2014
WO        2009036354 A2      3/2009

(Continued)

OTHER PUBLICATIONS

Akbulut et al., "Separation of Nanoparticles in Aqueous Multiphase Systems Through Centrifugation," Nano Letters, (2012), 12, (8), pp. 4060-4064.

(Continued)

*Primary Examiner* — Tabatha L Penny
(74) *Attorney, Agent, or Firm* — Cantor Colburn LLP (57) ABSTRACT

The present invention disclosed a continuous flow and batch process for the separation of metal or metal oxide nanoparticles continuously in a periodic manner at the liquid-liquid interface using a centrifugal separator cum extractor, wherein the nanoparticles are collected at the liquid-liquid interface of the polar and non-polar liquids.

14 Claims, 2 Drawing Sheets

(56) References Cited

U.S. PATENT DOCUMENTS

2011/0142743 A1 6/2011 Bol et al.
2015/0050727 A1* 2/2015 Edel .................. C12N 15/1006
435/320.1

FOREIGN PATENT DOCUMENTS

WO WO-2009036354 A2 * 3/2009 ............. B82Y 30/00
WO WO-2011126368 A1 * 10/2011 ............. A23P 10/35

OTHER PUBLICATIONS

Anders et al., "Tangential Flow Ultrafiltration: A Green Method for the Size Selection and Concentration of Colloidal Silver Nanoparticles," Journal of Visualized Experiments, 2012, (68): 4167, 9 pages.
Machunsky et al., "Liquid-Liquid Interfacial Transport of Nanoparticles," Physical Separation in Science and Engineering, (2007), Article ID 34832, 7 pages.
Qian et al., "Multiphase Separation of Copper Nanowires," Chemical Communications, (2016), 52, pp. 11627-11630.
Qiu et al., "Viscosity Gradient as a Novel Mechanism for the Cenliifugation-Based Separation of Nanoparticles," Advanced Materials, (2011); 23, (42), pp. 4880-4885.
International Search Report for International Application No. PCT/IN2018/050265; International Filing Date—Apr. 30, 2018; dated Aug. 14, 2018, 3 pages.
Written Opinion for International Application No. PCT/IN2018/050265; International Filing Date—Apr. 30, 2018; dated Aug. 14, 2018, 7 pages.

* cited by examiner

PROCESS FOR INTERFACIAL SEPARATION OF METAL NANOPARTICLES OR NANOWIRES USING CENTRIFUGAL SEPARATORS

CROSS REFERENCE TO RELATED APPLICATIONS

This application is a National Stage application of PCT/IN2018/050265, filed Apr. 30, 2018, which claims priority to India Application No. 201711007178, filed May 1, 2017, and all the benefits accruing therefrom under 35 U.S.C. § 119, the content of which is incorporated by reference in its entirety.

FIELD OF THE INVENTION

The present invention relates to a process for the separation of metal or metal oxide nanoparticles or nanowires continuously in a periodic manner at the liquid-liquid interface using a centrifugal separator cum extractor.

BACKGROUND AND PRIOR ART OF THE INVENTION

Nanoparticles exhibit remarkable electrical, optical, chemical and magnetic properties and the physic-chemical properties depend on their size and shape distributions. Therefore, obtaining nanoparticles of desired shape and size is critical and technological advancement is pursued by the researchers around the world to exploit their characteristic properties. Nanoparticles are typically produced at concentration of decigrams or grams per litre to avoid agglomeration issues. Various separation techniques including chromatography, magnetic separation, electrophoresis, selective precipitation, membrane filtration, solvent or solution-based extractions have been used for isolating nanoparticles.

Removal of excess solvent using heat or vacuum is also one of the techniques employed, however, using heat or vacuum for removing the solvent is not energy efficient and using fractionation columns is a very slow process which is not industrially feasible. Using membranes may involve difficulty in separating the particles lodged inside the membranes. Anti-solvent or electrochemistry based methods differ according from material to material used which makes the process cumbersome.

Tangential flow Ultrafiltration (TFU) which is a recirculation method is used to concentrate, separate and isolate proteins, viruses, cells and can be applied for separation of metal nanoparticles wherein the substance is tangentially passed across a filtration membrane with relatively low pressure. An article titled 'Tangential Flow Ultrafiltration: A Green Method for the Size Selection and Concentration of Colloidal Silver Nanoparticles' by Catherine B. Anders et. al published in Journal of visualized experiments, 2012, (68): 4167 discloses a 3-step TFU for the separation and concentration of silver nanoparticles. The final retentate consist of nanoparticles of concentration 8,539.9 µg ml$^{-1}$ with reduced aggregation. The process however results in very low concentration of nanoparticles.

Article titled "Multiphase separation of copper nanowires" by F Qian et al. published in *Chem. Commun.*, 2016, 52, pp 11627-11630 reports a new method to purify copper nanowires with nearly 100% yield from undesired copper nanoparticle side-products formed during batch processes of copper nanowire synthesis. They reports that the separation of nanowires from nanoparticles in which the desired product (nanowires) crosses the interface and sinks to the bottom wall. This simple separation method can yield large quantities of long, uniform, high-purity copper nanowires to meet the requirements of nanoelectronics applications as well as provide an avenue for purifying copper nanowires in the industrial scale synthesis of copper nanowires, a key step for commercialization and application of nanowires.

Article titled "Viscosity gradient as a novel mechanism for the centrifugation-based separation of nanoparticles" by P Qiu et al. published in *Adv. Mater.;* 2011; 23(42); pp 4880-5 reports viscosity gradient as a novel mechanism for the centrifugation-based separation of nanoparticles. A novel viscosity gradient, built by stacking aqueous solutions of polyvinylpyrrolidone (PVP), is introduced to achieve precise size separation of nanoparticles. The viscosity gradient is more powerful than the conventional density gradient in separating larger nanoparticles. Nanoparticles that aggregate in PVP solutions are successfully stabilized and separated by size.

The use of aqueous multiphase systems (MuPSs) as media for rate-zonal centrifugation to separate nanoparticles of different shapes and sizes is disclosed in an article titled 'Separation of nanoparticles in aqueous multiphase systems through centrifugation' by Ozge Akbulut et. al published in *Nano Lett.*, 2012, 12 (8), pp 4060-4064. The article discloses a three-phase system for separation of the reaction products (nanorods, nanospheres, and large particles) of synthesis of gold nanorods, and enriches the nanorods from 48 to 99% using a bench top centrifuge. The rate zonal separation also relies on density gradients.

Article titled "Liquid-liquid interfacial transport of nanoparticles" by S Machunsky et al. published in *Physical Separation in Science and Engineering.* 2007, Volume 2007, Article ID 34832, pages 7 reports transfer of nanoparticles from the aqueous phase to the second nonmiscible nonaqueous liquid phase. The transfer is based on the sedimentation of the dispersed particles through a liquid-liquid interface. First, the colloidal aqueous dispersion is destabilized to flocculate the particles. The agglomeration is reversible and the flocs are large enough to sediment in a centrifugal field. The aqueous dispersion is laminated above the receiving organic liquid phase. When the particles start to penetrate into the liquid-liquid interface, the particle surface is covered with the stabilizing surfactant. The sorption of the surfactant onto the surface of the primary particles leads to the disintegration of the flocs.

Centrifugation is a widely used technique to isolate suspended particles from their surrounding medium in either a batch or a continuous—flow basis. The particles can be both concentrated and purified under centrifugal forces. The centrifugal force generated by centrifugation is proportional to the speed of rotation and the radius of the rotor. When a suspension is rotated at a certain speed or revolutions per minute (RPM), centrifugal force causes the particles to move radially away from the axis of rotation. Forces generated as the rotor spins cause components in the sample to migrate toward the bottom or top of the sample tube, according to weight or density.

There are different types of centrifugal separations such as differential centrifugation, density gradient centrifugation which is further classified into rate zonal centrifugation or Isopycnic Centrifugation. The density gradient separation includes filling the tube with different concentrations of sucrose or another solute establishing layers with different densities and viscosities density gradient, within which the particles to be resolved are added and subjecting to high speed ultra-centrifugation. Rate-zonal centrifugation separates particles based on differences in their sedimentation coefficients (s), which is a function of both particle size and density. The isopycnic (or equilibrium buoyant density) separations, function on the principle of migration of particles through the density gradient until they reach the point at which their density is equal to that of the surrounding medium.

The crucial problem in the performance of density gradient centrifugation is the charging of the centrifugation vessel so as to ensure a clean interface between the lower body of working fluid and the upper body of liquid dispersion. Moreover, the density gradient centrifugation is not feasible on industrial scale since the narrow load zone limits the volume of the sample that can be accommodated on the density gradient. Further, when the centrifugal extractor is used only with the nanoparticle suspension, the nanoparticles adhere to the wall of the centrifuge. This phenomenon is particularly seen during batch centrifugation where the attached particles have to be removed by applying sonication.

During scale-up of nanomaterial separation, much larger volumes of suspension need to be produced. This can either be done in batch mode using large drum centrifuges or in continuous mode using annular centrifugal extractors. Industrial batch centrifuges are typically designed for separating out large cakes of denser materials from liquids. It is difficult to utilize these separators directly for separating nanomaterials. They typically have a rotor of up to 65 inches in diameter and separation zones which are about 30 inches wide. While the material near the outer wall of the separation zone settles immediately at the outer wall, the material close to the rotor takes a long time to reach outer wall. At the end of the operation, a hard thin layer is formed. Since nanomaterials are produced in low concentrations, the deposition is typically only a thin film of a few microns at best. Sonication is impractical on the large scale, and these centrifuges typically use mechanical operations like scraping/scrubbing separating the cake. These methods are not efficient for removing nanomaterials films of a few microns. The nanomaterials thin films must instead be handled with precision and any crude operation can lead to loss of the valuable thin film. At the same time, from a process point of view, removal of the thin film should also be carried out as quickly as possible in order to reduce the centrifuge downtime. In case of a continuous operation, the issues are worse since deposition inside the centrifuge cannot be recovered without opening the centrifuge. It is hence necessary to devise a method which can separate the film quickly and precisely with minimal losses for both batch and continuous modes of operation.

With a view to operate the separation of metal nanoparticles wherein large volumes of the material can be centrifuged at high centrifugal forces, preventing the deposition of the nanoparticles on to the side walls of the centrifuge, isolating the nanoparticles in periodic manner with enhanced concentration there remains a need to provide a more efficacious process for separation of nanoparticles that can meet the challenges of the art.

Objective of the Invention

Accordingly, the main objective of the present invention is to provide a process for the separation of metal or metal oxide and other inorganic nanoparticles or nanowires without agglomeration using one or more centrifugal extractors and in batch separators with minimum deposition at the wall, maximum recovery and minimum downtime.

SUMMARY OF THE INVENTION

Accordingly, the present invention provides a process for the interfacial separation of metal or metal oxide nanoparticle or nanowires using one or more centrifugal extractor cum separator comprising continuously feeding the centrifuge with a suspension of metal or metal oxide nanoparticles or nanowires in a polar or non-polar solvent along with a stabilizer and an inert organic polar or non-polar solvent, wherein said inert solvent is immiscible in the suspension, centrifuging at desired rotational speed (rpm) and removing the concentrated metal or metal oxide nanoparticles in gel form from the liquid-liquid interface.

In preferred embodiment, the interfacial separation process of the present invention is carried out in batch mode or continuous flow mode.

The metal or metal oxide nanoparticle or nanowires are selected from the metals such as silver (Ag), Gold (Au), Iron (Fe), Cobalt (Co), Copper (Cu), Nickel (Ni), Platinum (Pt), Palladium (Pd), Ruthenium (Ru), Rhodium (Rh) either in metallic form or their oxides with average diameter in the range of 80-1000 nm.

The present invention provides use of a liquid-liquid interfacial tension to collect the nanoparticles in the said centrifugation process. The present invention further provides a process for the enhancement of the recovery of nanoparticles by adding specific amount of anti-solvent in the centrifuge.

DETAILED DESCRIPTION OF THE INVENTION

The present invention will now be described in preferred as well as optional embodiments so that the various aspects disclosed therein will be more clearly understood and appreciated.

In view of the above, the present invention provides a process for the separation of metal or metal oxide nanoparticles or nanowires using one or more centrifugal extractor cum separator, wherein, the nanoparticles are collected at the liquid-liquid interface of the polar and non-polar liquids. The liquid-liquid interfacial tension created during the centrifugation avoids the deposition of the metal nanoparticles at the wall of the centrifuge due to the centrifugal force. The particles are held at the liquid-liquid interface which results in the formation of concentrated middle layer inside the centrifuge which are removed by freezing the operation and draining the liquid or varying the flow rates of the two liquids.

In an embodiment, the present invention provides a process for interfacial separation of metal or metal oxide nano particles or nanowires for obtaining concentrated gel using one or more centrifugal extractor cum separator comprising continuously feeding the centrifuge with suspension of metal or metal oxide nanoparticles or nanowires in polar or non-polar solvent along with stabilizer and an inert organic polar or non-polar solvent, centrifuging at desired rotational speed (rpm) and removing the concentrated metal or metal oxide nanoparticles or nanowires in gel form from the liquid-liquid interface, wherein said inert solvent is immiscible in the suspension.

In preferred embodiment of the present invention, the process for the interfacial separation of metal or metal oxide nano particles or nanowires is carried out in batch mode. In another preferred embodiment of the present invention, the process for the interfacial separation of metal or metal oxide nano particles or nanowires is carried out in continuous flow mode.

The various metal, metal oxide or other inorganic materials or metal nanoparticles or metal nanowires can be separated at the liquid-liquid interface by using this invention. The size of the particle and the density of the particle decide how much force they exert at the interface. If this force is small the interfacial tension of the two liquids is enough to balance it. If this force is high, then the nanoparticle surfaces can be capped with a hydrophilic stabilizer which has low solubility in the organic denser phase. This makes the denser phase molecules repel the material since it has non-wetting surfaces. This molecular force then acts along with the surface tension in order to balance the centrifugal force. Preferably, the nanoparticles are selected from the metals such as silver (Ag), Gold (Au), Iron (Fe), Cobalt (Co), Copper (Cu), Nickel (Ni), Platinum (Pt), Palladium (Pd), Ruthenium (Ru), Rhodium (Rh) either in metallic form or their oxides with average diameter in the range of 80-1000 nm. More preferably, the nanoparticles are silver nanoparticles.

The nanowires are selected from the metals such as silver (Ag), Gold (Au), Iron (Fe), Cobalt (Co), Copper (Cu), Nickel (Ni), Platinum (Pt), Palladium (Pd), Ruthenium (Ru), Rhodium (Rh) either in metallic form or their oxides with average diameter in the range of 80-1000 nm. More preferably, the nanoparticles are silver nanowires.

The polar or non-polar solvents to disperse the metal or metal oxide nano particle or nanowire are selected with sufficiently low density such as water, toluene, xylene, aliphatic hydrocarbons and the like; preferably water. The immiscible inert organic polar or non-polar solvent of comparative high density is selected from solvent grade chloroform, dichloroethane, cyclohexane and the like; preferably solvent grade chloroform.

The stabilizer is selected from trisodium citrate, polyvinyl pyrrolidone (M.W 40,000), sodium alginate, glycol chitosan, polyvinyl alcohol (PVA) and the like to prevent agglomeration of the nanoparticles; preferably the stabilizer is polyvinyl pyrrolidone (M.W 40,000). The concentration of the stabilizer used ranges from 2.0 mmol-4.0 mmol.

The centrifugation process of the present invention is independent of particle size, shape, mass or composition of the metal or metal oxide, the suspension can be mono dispersed or polydispersed. The rotational speed (rpm) of the centrifuge can be adjusted or tuned according to the particle size and its distribution. In one of the embodiment, the rotational speed of the centrifuge is in the range 6000 rpm to 20000 rpm.

In a preferred embodiment, the continuous interfacial separation of metal or metal oxide nanoparticles using a centrifugal extractor comprises passing the suspension of silver nanoparticles of concentration in the range of 80-1000 ppm in water followed by adding PVP (MW 40,000) as stabilizer into the centrifugal extractor at a flow rate of 2-4 ml/min and the solvent grade chloroform at a flow rate of 2-10 ml/min continuously. The change in colour of the aqueous layer confirmed by UV-Vis indicates the absence of the nanoparticles in said layer. A thin dark layer at the liquid-liquid interface indicates the presence or capture of the significant proportion of silver nanoparticles. It is observed that, there is no shiny silver layer at the interface which confirmed that there is no agglomeration. The concentrated silver nanoparticles coated with PVP in gel form are removed intermittently by removing the liquids followed by drying the mass.

The concentrated silver nanoparticles formed in the middle layer inside the centrifuge are removed by freezing the operation and draining the liquid or varying the flow rates of the two liquids. No further agglomeration is observed upon drying and complete re-dispersibility is observed. More than 95% of PVP is recovered in the aqueous layer which is recycled and reused.

Adding specific amounts of liquid which reduces the density and viscosity of the medium improves the settling velocity slightly. If this liquid also acts as an anti-solvent to the stabilizer which coats the particles, the settling velocity is seen to show a significant increase. An example case for PVP stabilized aqueous suspensions can be a standalone low boiling organic solvent (viz. acetone, ethyl acetate, n-pentane, dichloromethane, etc.) or a mixture thereof which destabilizes the excess PVP dissolved in the aqueous media thereby displacing it from aqueous phase along with the encapsulated nanoparticles. This also reduces the density and viscosity of water.

It is observed that increasing the temperature reduces the viscosity and accelerates particle settling. Such variation is more important in the case of viscous liquids like oils and glycols which show rapid change in viscosity with temperature thus allowing centrifugal separation in these viscous phases. The upper limits of temperature and anti-solvent concentration are controlled by the corresponding reduction caused in the interfacial tension by these factors.

The present invention provides a method in which nanoparticles can be made to stay at the interface due to the balance of centrifugal force and the miscibility of the surfactant in the denser inert phase. PVP has limited solubility in chloroform and thus restricts the entry of nanoparticles into the chloroform phase. However, with extended time, slowly some PVP dissolves into the chloroform phase based on its diffusivity. The separation at the interface is hence possible only if the settling time is faster than the mass transfer time. If the settling time is very small in comparison, then separation at interface can be carried out in a single stage operation with minimal loss at the interface. If settling is moderately faster than the diffusion of surfactant, then the operation is to be partly carried out in a single stage and then halted before loss of nanoparticles due to diffusion will occur. The remaining nanoparticles must then be separated in the second stage and so on. The number of continuous flow centrifuges required can thus be calculated from the stage efficiency in batch.

In one embodiment of the present invention, the interfacial separation of metal or metal oxide nanoparticles or nanowires in a centrifugal extractor may be performed batch wise.

In a preferred embodiment, the batch centrifugation process for interfacial separation of metal or metal oxide nanoparticles using a centrifugal separator comprises 100 ppm colloid of 60-90 nm citrate capped silver nanoparticles is mixed with PVP (K30, molecular weight: 40,000) till the PVP concentration reached 13% (by weight). The colloid is introduced in an Eppendorf tube along with 1 ml pure chloroform and mixed vigorously by sonication for 10 mins. The Eppendorf is later subjected to centrifugation at varying g-force. In this case silver nanoparticles formed a thick brown layer at the interface which is removed, dried and redispersed to form the original nanoparticle colloid. During the settling operation, mass transfer of PVP coated on already settled nanoparticles also occurred as function of the mass transfer coefficient. This resulted in the particles being slowly stripped of their PVP coating. If this is allowed to occur by continuing the centrifugation over an extended period of time, the nanoparticles agglomerated at the interface. The amount of redispersible mass at the interface at various times is calculated by isolating the cake (removing both the liquids) and redispersing the cake in 1 ml DI water. The results are shown in FIG. 2.

Figure 1:
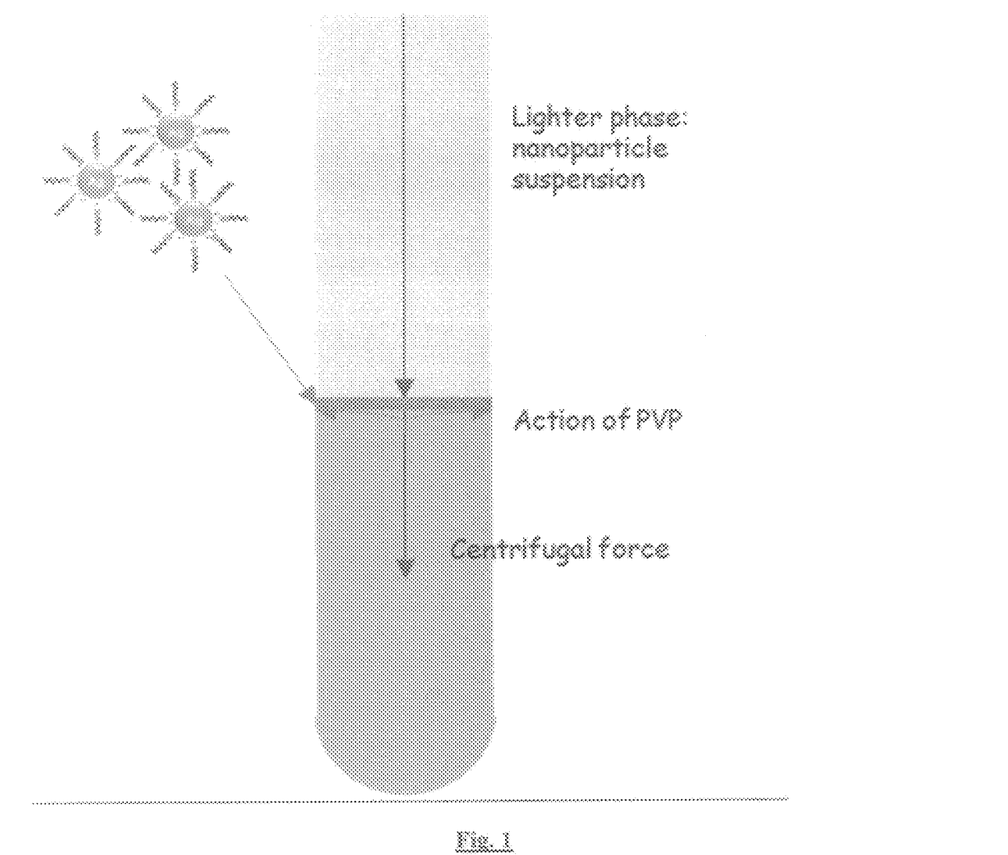
FIG. 1: A diagram showing the concept of the invention in terms of settling PVP capped silver nanoparticles (a) Lighter phase: nanoparticle suspension (b) action of PVP (c) centrifugal force.
Figure 2:
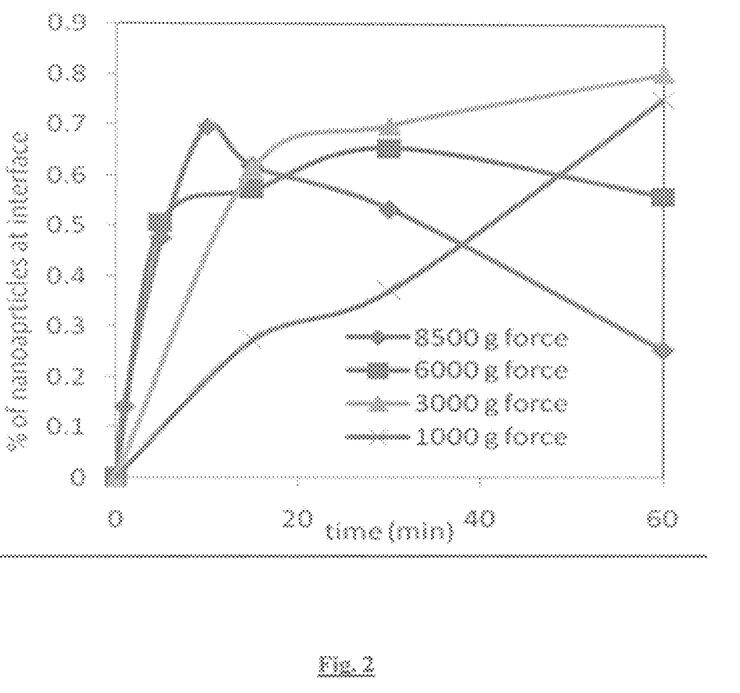
FIG. 2: shows percentage of total nanoparticles retained at the interface.

Based on the decline in concentration of nanoparticles shown in FIG. 2 (due to agglomeration caused by mass transfer of PVP), the overall mass transfer coefficient of PVP is changed. The value is estimated as a constant ~0.00051/s that helps in predicting all the curves shown in FIG. 2. This means the mass transfer time for PVP roughly ranged around 2000 s. According to conventional chemical engineering thumb rules, a settling time of 200 s is desirable for a single stage operation (i.e. for minimal losses) in order to at 8500 g-force, the settling time is ~600 s and it is observed that about 70% of the nanoparticles are recovered at the interface while the rest are lost.

The batch centrifugation is carried out at 8500 g-force for only 200 s. The supernatant liquid is then removed followed by injected and mixed into another eppendorf tube with a fresh chloroform solvent of equal volume. The eppendorf is again centrifuged at 8500 g-force for 200 s. This operation represents the second stage. A third stage is carried out in a similar fashion to complete the 600 s required for separation of the nanoparticles. Total recovery of nanoparticles from the three stages combined is around 94%. Recovery can be enhanced further by increasing the number of stages.

In the process of continuous flow centrifuge (CINC V02, g-force at wall: 1000) the AgNP colloid with 13% PVP is introduced along with chloroform in 1:1 volume ratio into the centrifuge. The centrifuge is operated at a maximum possible residence time of 30 mins and with a maximum possible g-force at the wall=1000. The operation was halted after 60 mins and all the contents are drained. The liquid-liquid interface is collected separately. ~30% AgNP recovery is obtained from the liquid-liquid interface. The predicted recovery is between 40-45%. The model overpredicted the recovery slightly, since it considered the overall mass transfer coefficient of PVP obtained from batch experiments. Certainly, due to continuous rotation and shearing inside the continuous flow centrifugal extractor, the mass transfer coefficient will be higher than that obtained from the batch operation. While this will increase the number of stages required for separation, this is not exactly a disadvantage since the objective of separation methods for nanoparticles is not to simply concentrate the nanoparticles but also to wash off and recover the surplus surfactant. For examples, in the above case, washing off the PVP coating of the silver nanoparticles improved their antibacterial activity significantly (table 2 below) and conductivity also increased (over a range of 2-200% when compared to PVP coated particles), thus increasing the functionality and value addition of the material. In short, the disclosed method can use the balance of diffusion of surfactant and centrifugal force to not only concentrate the nanoparticles but also wash them in order to increase their functionality. It is understood that this balance of washing and concentration is only possible when the settling time and mixing time is comparable. When settling time is higher the separation efficiency can be increased significantly, but the washing operation will not be so efficient (Table 1 below). Thus the nanoparticles of particle size in the range of 80-120 nm are thought to represent the best range for application of this method for both washing and separation. However, for separation alone, this method can be used most effectively in the case of micron sized nanoparticles.

TABLE 1

Comparison of separation efficiencies for various nanoparticles sizes

| Nanoparticle size (nm) | Separation efficiency (%) | Separation time (minutes) |
| --- | --- | --- |
| 90 | 60 | 45 |
| 120 | 72 | 28 |
| 150 | 80 | 17 |
| 200 | 90 | 11 |
| 300 | 95 | 5 |
| 500 | 98 | 2 |
| 1000 | 99 | 1 |

TABLE 2

Comparison of antibacterial activities of PVP capped silver nanoparticles after washing the 13% PVP 100 AgNP suspension upto 4 times. The amount of PVP capping the nanoparticles is given in percentages.

| MIC (ppm) → Bacteria ↓ | 8% PVP 1000 ppm silver (one wash) | 4% PVP 1000 ppm silver (2 washes) | 1% PVP 1000 ppm silver (3 washes) | 0.1% PVP 500 ppm silver (4 washes) | PVP stabilizer |
| --- | --- | --- | --- | --- | --- |
| E.coli | 600 | 300 | 300 | 150 | 0.0 |
| S.enterica | 400 | 500 | 400 | 300-400 | 0.0 |
| A.junii | 600 | 500 | 500 | Not tested | 0.0 |
| B.subtilis | ~0.0 | 0.0 | 0.0 | 0.0 | 0.0 |
| S.aureus | ~0.0 | 0.0 | 0.0 | 0.0 | 0.0 |

Thus by using a continuous centrifugal extractor and isolating the particles in a periodic manner from the interface while the aqueous and organic phase flow continuously, concentration enhancement by as much as 1000 times can be achieved along with enhancement of functionality of the material depending upon the residence time in the centrifugal separator.

Following examples are given by way of illustration therefore should not be construed to limit the scope of the invention.

Example 1: Batch Centrifugation of Silver Nanoparticles without PVP 1 ml of 100 ppm suspension of silver nanoparticles of average diameter in the range of 90 to 120 nm is taken in an eppendorf tube. To this is added trisodium citrate (3 mmol) as stabilizer. 0.5 ml of solvent grade chloroform is introduced into the eppendorf tube. The eppendorf tube is then centrifuged at 13,000 rpm in a laboratory micro centrifuge for a period of about 10 minutes. Distance from the centre of the centrifuge is approx. 12-15 cm such that g-force at the interface of the 2 immiscible liquids of the tube is $2 \times 10^6$ G·s. After completion of operation it is observed that the aqueous layer loses its colour indicating the absence of nanoparticles in the aqueous layer which is further confirmed by UV-Vis. A thin dark layer at the liquid-liquid interface shows the presence of silver nanoparticles at the interface. Since citrate is a very labile group and its concentration is very low, the nanoparticles are held at the interface due to the surface tension at the interface and this prevents the nanoparticles from crossing over to the chloroform phase. Sonicating the interface layer re-disperses about 20% of the actual nanoparticles as determined by UV-Vis. Thus 80% of nanoparticles were lost to the chloroform phase or to irreversible agglomeration. A red shift in the UV-Vis is also observed confirming that the particle size has increased due to aggregation. The presence of a shiny silver material at the interface confirms that the remaining silver nanoparticles have agglomerated to form much larger structures. This is attributed to the fact that the nanoparticles are closely stacked at the interface. The two immiscible fluids are removed almost completely and the remaining mass is dried. Complete agglomeration takes place and no re-dispersibility is observed.

Example 2: Batch Centrifugation of Silver Nanoparticles with PVP 1 ml of 100 ppm suspension of silver nanoparticles of average diameter in the range of 90 to 120 nm is taken in an eppendorf tube. To this is added polyvinyl pyrrolidone (MW 40,000) as stabilizer such that concentration of PVP in the solution is 13% by weight (2 mMol). 1 ml of chloroform suspension is added to the eppendorf tube and the centrifuge tube is shaken vigorously for dissolution of the two phases. The centrifuge tube is then centrifuged at 13,000 rpm in a laboratory centrifuge for about 10 minutes. Distance from the centre of the centrifuge is maintained at 12-15 cm such that g-force at the liquid-liquid interface is about 8500 g. After the operation, the nanoparticles are collected at the liquid-liquid interface. The low miscibility of PVP in chloroform prevents the nanoparticles from entering the chloroform phase. Sonicating the interface layer in fresh DI water redisperses about 70% of the AgNPs as determined by UV-Vis. No red/blue shift in the UV-Vis spectra is observed. The collected slurry is dried to form a flaky powder with no agglomeration and complete re-dispersibility is observed.

Example 3: Batch Centrifugation with PVP Using Multiple Stages 1 ml of 100 ppm suspension of silver nanoparticles of average diameter in the range of 90 to 120 nm is taken in an eppendorf tube. To this is added of polyvinyl pyrrolidone (MW 40,000) as stabilizer such that concentration of PVP is 13% by weight (2 mMol). 1 ml of chloroform suspension is added to the eppendorf tube and the centrifuge tube is shaken vigorously for dissolution of the two phases. The centrifuge tube is then centrifuged at 13,000 rpm in a laboratory centrifuge for about 3 minutes. Distance from the centre of the centrifuge is maintained at 12-15 cm such that g-force at the liquid-liquid interface is about 8500 g. After the operation, the nanoparticles are collected at the liquid-liquid interface. The low miscibility of PVP in chloroform prevents the nanoparticles from entering the chloroform phase. This operation is repeated 4 times. The contents of the centrifuge tubes are mixed together. The material at the liquid-liquid interfaces is now combined at a single interface. It is then redispersed in 1 ml DI water by sonication showing 90-94% recovery of silver nanoparticles. Thus using multiple stages improves the recovery of nanoparticles.

Example 4: Continuous Interfacial Centrifugation 100 ppm suspension of citrate stabilized silver nanoparticles of average diameter in the range of 90 to 120 nm is passed into a continuous flow centrifugal extractor (CINC V02, 200 ml volume) at a flow rate of 2 ml/min. Solvent grade chloroform is further introduced into the centrifugal extractor at flow rate of 2 ml/min. The rpm of the motor is tuned to create 1000 G force at the wall of the centrifuge. Distance from the centre of the centrifuge is maintained at 12-15 cm such that g-force at the interface of the two immiscible liquids of the tube is $2\times10^6$ G·s. The aqueous layer shows reduction in colour indicating the absence of nanoparticles in the aqueous layer (85% of particles are lost from the aqueous layer as confirmed by UV-Vis). A thin dark layer at the liquid-liquid interface indicating the presence of agglomerated silver nanoparticles at the interface. The layer contains shiny silver flakes indicating agglomeration. Sonicating this layer re-disperses about 10% of the actual nanoparticles.

Example 5: Continuous Interfacial Recovery and Continuous Centrifugation

A suspension of 100 ppm silver nanoparticles (of average diameter in the range of 90 to 120 nm) in water and of polyvinyl pyrrolidone (MW 40,000) is passed into a continuous flow centrifugal extractor at a flow rate of 2 mli/min. Solvent grade chloroform is introduced into the centrifugal extractor at flow rates of 2-10 ml/min. The rpm of the motor is tuned so as to create 1000 g-force at the wall of the centrifuge. Distance from the centre of the centrifuge is maintained approx.12-15 cm such that g-force at the interface of the two immiscible liquids of the tube is $2\times10^6$ G·s. About 10-20% of the PVP dissolves in the chloroform layer while the colour of the aqueous layer reduces significantly indicating the absence of nanoparticles in the aqueous layer (about 85% of the particles from the aqueous layer are lost confirmed by UV-Vis). A thin dark viscous layer at the liquid-liquid interface captures significant proportion of the silver nanoparticles at the interface. Sonicating this layer re-disperses about 70% of the deposited actual nanoparticles as determined by UV-Vis. No presence of shiny silver layer at the interface confirms that there is no agglomeration. The presence of dark black flakes in the chloroform phase which are not re-dispersible shows that maintaining a specific value of G·s is required for separation and the agglomeration is observed due to the larger residence time. A residence time of 45 mins leads to a loss of more than about 35% or more of the nanoparticles due to agglomeration. A residence time of ~ 15 mins with 3 centrifuges operated in series gives nearly the batch equivalent (80-90%) recovery of re-dispersible nanoparticles. The two immiscible fluids are removed almost completely and the remaining mass is dried. Complete re-dispersibility with no further agglomeration is observed upon drying. More than 95% of PVP is recovered in the aqueous layer which is recycled and reused.

Example 6A: Batch Centrifugation of Silica Particles without PVP 1 ml of 100 ppm suspension of silica nanoparticles of average diameter in the range of 1 micron is taken in an eppendorf tube. 0.5 ml of solvent grade chloroform is introduced into the eppendorf tube. The eppendorf tube is then centrifuged at ~2000-4000 rpm in a laboratory micro centrifuge for <1 minutes. Distance from the centre of the centrifuge is approx. 12-15 cm. After completion of operation it is observed that the aqueous layer loses its turbidity indicating the absence of silica particles in the aqueous layer. A thin white layer at the liquid-liquid interface shows the presence of silica nanoparticles at the interface. ~85% of the particles are held at the interface due to the surface tension at the interface while about ~15% of particles settle at the bottom of the eppendorf tube in the chloroform phase. Sonicating the interface layer re-disperses all the particles that have settled at the interface. The layer at the interface can be removed and dried separately to recover 85% of the silica material.

Example 6B: Continuous Centrifugation of Silica Particles without PVP

For the concentration of silica nanoparticles as in Example 6A, is passed into a continuous flow centrifugal extractor at a flow rate of 2 m/min. The flow rate of chloroform and the rpm of the motor were maintained as in Example 5. The aqueous phase coming out of the continuous flow centrifugal extractor was almost clear while the chloroform phase was found to have some turbidity. Upon operating the continuous flow centrifugal extractor for two hours at a residence time of 10 min for both the phases, a thick white layer of silica particles was recovered that got accumulated at the interface.

Example 7: Batch Centrifugation of Silica Particles with PVP 1 ml of 100 ppm suspension of silica nanoparticles in water of average diameter in the range of 1 micron is taken in an eppendorf tube. PVP is mixed into this suspension such that its final concentration is ~13% by weight. 0.5 ml of solvent grade chloroform is introduced into the eppendorf tube. The eppendorf tube is then centrifuged at ~2000-4000 rpm in a laboratory micro centrifuge for <1 minutes. Distance from the centre of the centrifuge is approx. 12-15 cm. After completion of operation it is observed that the aqueous layer loses its turbidity indicating the absence of silica particles in the aqueous layer. A thin white layer at the liquid-liquid interface shows the presence of silica nanoparticles at the interface. ~85-90% of the particles are held at the interface due to the surface tension at the interface while about ~10-15% of particles settle at the bottom of the eppendorf tube in the chloroform phase. Sonicating the interface layer re-disperses all the particles that have settled at the interface. The layer at the interface can be removed and dried separately to recover 85-90% of the silica material. Therefore the method still separates silica nanoparticles at the liquid-liquid interface under the action of centrifugation. However, in this case, since low density material like silica is used (density of water=1 g/cc, density of silica=2.6 g/cc, density of silver=10.5 g/cc), the effect of adding PVP is negligible and the balance between surface tension and centrifugal force is enough for separation and is primarily responsible for the collection at the interface.

Example 8: Batch Centrifugation of Copper Oxide Particles

For the conditions given in Example 7, an aqueous suspension of large copper oxide particles of average diameter in the range of hundreds of microns was used and subjected to centrifugation as in Example 7. A thin black layer at the liquid-liquid interface shows the presence of copper oxide particles at the interface. <10% of the particles are held at the interface and all the rest precipitate to the bottom of the tube in the chloroform phase.

Example 9A: Batch Centrifugation of Copper Oxide Nanoparticles

For the composition as given in Example 8, upon centrifugation at ~13000 rpm in a laboratory micro centrifuge for >30 minutes, the amount of copper oxide lost to the chloroform phase is between 1-2% and ~98-99% of the particles are held at the interface. The amount of copper oxide lost is less as compared to the loss of silver nanoparticles.

Example 9B: Continuous Centrifugation of Copper Oxide Nanoparticles

For the concentration of copper oxide nanoparticles as in Example 9A, the suspension is passed into a continuous flow centrifugal extractor at a flow rate of 2 ml/min. The flow rate of chloroform and the rpm of the motor were maintained as in Example 5. The aqueous phase coming out of the continuous flow centrifugal extractor was having little brownish tinch indicating very little amount of particles remained suspended in the solution, while the chloroform phase was slightly brown. Upon operating the continuous flow centrifugal extractor for two hours at a residence time of 10 min for both the phases, a thick dark layer of copper oxide particles was recovered that got accumulated at the interface.

Example 10A: Batch Centrifugation of Silver Nanowires with PVP 1 ml of 400 ppm suspension of silver nanowires in ethylene glycol of average diameter <50 nm and length of ~20 microns is taken in an eppendorf tube. PVP is mixed into this suspension such that its final concentration 0.613 g/L. 0.5 ml of solvent grade chloroform is introduced into the eppendorf tube. The eppendorf tube is then centrifuged at ~13000 rpm in a laboratory micro centrifuge for ~1-2 minute. After completion of operation it is observed that the aqueous layer loses its whitish-grayish colour indicating the absence of silver nanowires in the aqueous layer. A thin greenish-gray layer at the liquid-liquid interface shows the presence of silver nanowires at the interface. The amount of silver nanowires lost to the chloroform phase is between 1-2% and ~98-99% of the nanowires are held at the interface in form of a thin layer. Sonicating the interface layer re-disperses all the nanowires that have settled at the interface. The layer at the interface can be removed and dried separately to recover ~98-99% of the silver nanowires. In this case, the nanowires are not only sufficiently dense but they also have a large net mass. For centrifugation time is between 1-2 minutes, only 1-2% loss of particles to chloroform phase was observed.

Example 10B: Continuous Centrifugation of Silver Nanowires with PVP

For the concentration of silver nanowires as in Example 10A, the suspension is passed into a continuous flow centrifugal extractor at a flow rate of 5 m/min. The flow rate of chloroform and the rpm of the motor were maintained as in Example 5. The aqueous phase coming out of the continuous flow centrifugal extractor was clear indicating almost no remaining traces of nanowires suspended in the solution, while the chloroform phase was slightly gray. Upon operating the continuous flow centrifugal extractor for two hours at a residence time of 10 min for both the phases, a thick gray layer of silver nanowires was recovered, which was found accumulated at the interface. This layer could be sonicated and redispersed to make solutions of any concentration.

Advantages of the Invention

The present invention provides interfacial separation of metal or metal oxide nanoparticles in continuous manner using centrifugal separator/extractor wherein concentration enhancement by as much as 1000 times without agglomeration can be achieved depending upon the residence time in the centrifugal separator. The present invention discloses a process separation of nanomaterials at the interface inside a continuous flow centrifuge as a balance of miscibility of the surfactant and centrifugal force exerted on the nanomaterials. This is important from a process point of view in continuous flow since nanomaterials get deposited irreversibly on wall of continuous flow centrifuge if they cross the interface. While depositions can be removed in batch while charging/discharging, it is impossible to remove depositions in continuous flow without disassembly which is very difficult and time consuming and uneconomical.

The invention claimed is:

1. A process for an interfacial separation of metal nanoparticles, metal oxide nanoparticles, metal nanowires, or metal oxide nanowires, the process comprising:
   using one or more centrifugal extractor cum separator;
   continuously feeding the one or more centrifugal extractor cum separator with an aqueous phase, wherein the aqueous phase comprises a suspension of the metal nanoparticles, the metal oxide nanoparticles, the metal nanowires, or the metal oxide nanowires, in a polar or a non-polar solvent along with a stabilizer, wherein concentration of the stabilizer is in a range from 2.0 mmol to 4.0 mmol;
   continuously feeding the one or more centrifugal extractor cum separator with an organic phase, wherein the organic phase comprises an inert organic polar or a non-polar solvent, and wherein flow rates of the aqueous phase and the organic phase are in a ratio of 1:5;
   centrifuging at a rotational speed (rpm) to create a 1000 g-force at walls of the one or more centrifugal extractor cum separator, wherein the metal nanoparticles, the metal oxide nanoparticles, the metal nanowires, or the metal oxide nanowires are held at an interface between the aqueous and the organic phase forming a concentrated middle layer inside the one or more centrifugal extractor cum separator; and
   periodically pausing the continuous feed and centrifuging to remove the concentrated middle layer comprising metal nanoparticles, metal oxide nanoparticles, metal nanowires, or metal oxide nanowires in a periodic manner in a gel form at a liquid-liquid interface.

2. The process as claimed in claim 1, wherein said metal nanoparticles, metal oxide nanoparticles, metal nanowires, or metal oxide nanowires, are selected from silver (Ag), Gold (Au), Iron (Fe), Cobalt (Co), Copper (Cu), Nickel (Ni), Platinum (Pt), Palladium (Pd), Ruthenium (Ru), Rhodium (Rh) with an average diameter ranging from 80-1000 nm.

3. The process as claimed in claim 1, wherein said metal nanoparticles are silver nanoparticles and metal nanowires are silver nanowires.

4. The process as claimed in claim 1, wherein said polar or non-polar solvent is selected from water, toluene, xylene, or aliphatic hydrocarbons.

5. The process as claimed in claim 1, wherein said inert organic polar or non-polar solvent is selected from chloroform, dichloroethane or cyclohexane.

6. The process as claimed in claim 1, wherein said stabilizer is selected from trisodium citrate, polyvinyl pyrrolidone (PVP), sodium alginate, glycol chitosan or Polyvinyl alcohol (PVA).

7. The process as claimed in claim 1, wherein said stabilizer is polyvinyl pyrrolidone.

8. A process for an interfacial separation of metal nanoparticles, metal oxide nanoparticles, metal nanowires, or metal oxide nanowires, the process comprising:
   using one or more centrifugal extractor cum separator;
   continuously feeding the one or more centrifugal extractor cum separator with an aqueous phase, wherein the aqueous phase comprises a suspension of the metal nanoparticles, the metal oxide nanoparticles, the metal nanowires, or the metal oxide nanowires, in a polar or a non-polar solvent along with a stabilizer, wherein concentration of the stabilizer is in a range from 2.0 mmol to 4.0 mmol;
   continuously feeding the one or more centrifugal extractor cum separator with an organic phase, wherein the organic phase comprises an inert organic polar or a non-polar solvent, and wherein flow rates of the aqueous phase and the organic phase are in a ratio of 1:5;
   centrifuging at a rotational speed (rpm) to create a 1000 g-force at walls of the one or more centrifugal extractor cum separator, wherein the metal nanoparticles, the metal oxide nanoparticles, the metal nanowires, or the metal oxide nanowires are held at an interface between the aqueous and the organic phase forming a concentrated middle layer inside the one or more centrifugal extractor cum separator; and
   periodically pausing the continuous feed and discharging to remove the concentrated middle layer comprising metal nanoparticles, metal oxide nanoparticles, metal nanowires, or metal oxide nanowires in a periodic manner in a gel form at a liquid-liquid interface, wherein 60-99% the metal nanoparticles, the metal oxide nanoparticles, the metal nanowires, or the metal oxide nanowires and about 95% of the stabilizer are recovered.

9. The process as claimed in claim 8, wherein said metal nanoparticles, metal oxide nanoparticles, metal nanowires, or metal oxide nanowires, are selected from silver (Ag), Gold (Au), Iron (Fe), Cobalt (Co), Copper (Cu), Nickel (Ni), Platinum (Pt), Palladium (Pd), Ruthenium (Ru), Rhodium (Rh) with an average diameter ranging from 80-1000 nm.

10. The process as claimed in claim 8, wherein said metal nanoparticles are silver nanoparticles and metal nanowires are silver nanowires.

11. The process as claimed in claim 8, wherein said polar or non-polar solvent is selected from water, toluene, xylene, or aliphatic hydrocarbons.

12. The process as claimed in claim 8, wherein said inert organic polar or non-polar solvent is selected from chloroform, dichloroethane or cyclohexane.

13. The process as claimed in claim 8, wherein said stabilizer is selected from trisodium citrate, polyvinyl pyrrolidone (PVP), sodium alginate, glycol chitosan or Polyvinyl alcohol (PVA).

14. The process as claimed in claim 8, wherein said stabilizer is polyvinyl pyrrolidone.

* * * * *